(12) United States Patent
Martens (10) Patent No.: US 7,882,742 B1
(45) Date of Patent: Feb. 8, 2011

(54) APPARATUS FOR DETECTING, IDENTIFYING AND RECORDING THE LOCATION OF DEFECTS IN A RAILWAY RAIL

(75) Inventor: George D. Martens, New Milford, CT (US)

(73) Assignee: Herzog Services, Inc., St. Joseph, MO (US)

( * ) Notice: Subject to any disclaimer, the term of this patent is extended or adjusted under 35 U.S.C. 154(b) by 304 days.

(21) Appl. No.: 12/260,059

(22) Filed: Oct. 28, 2008

(51) Int. Cl.
*G01N 29/24* (2006.01)
*G01N 29/28* (2006.01)
*G01N 29/265* (2006.01)

(52) U.S. Cl. .............. 73/636; 73/632; 73/633; 73/635; 73/644

(58) Field of Classification Search ............ 73/636, 73/602, 632, 633, 635, 639, 644
See application file for complete search history.

(56) References Cited

U.S. PATENT DOCUMENTS

| | | | |
|---|---|---|---|
| 3,771,354 A | 11/1973 | Miller | |
| 3,937,068 A * | 2/1976 | Joy | 73/636 |
| 3,962,908 A * | 6/1976 | Joy | 73/636 |
| 4,044,594 A * | 8/1977 | Owens et al. | 73/621 |
| 4,165,648 A | 8/1979 | Pagano | |
| 4,174,636 A | 11/1979 | Pagano | |
| 4,235,112 A | 11/1980 | Kaiser | |
| 4,429,576 A | 2/1984 | Norris | |
| 4,457,178 A | 7/1984 | Turbe et al. | |
| 4,468,966 A | 9/1984 | Bradshaw | |
| 4,487,071 A | 12/1984 | Pagano et al. | |
| 4,532,796 A | 8/1985 | Martens et al. | |
| 4,559,825 A | 12/1985 | Martens | |
| 4,593,569 A | 6/1986 | Joy | |
| 4,662,224 A | 5/1987 | Turbe | |
| 4,700,574 A | 10/1987 | Turbe | |
| 5,020,371 A | 6/1991 | Panetti | |
| 5,339,692 A * | 8/1994 | Shoenhair et al. | 73/636 |
| 5,419,196 A | 5/1995 | Havira et al. | |
| 5,578,758 A * | 11/1996 | Havira et al. | 73/636 |
| 5,654,510 A * | 8/1997 | Schneider | 73/622 |
| 6,055,862 A | 5/2000 | Martens | |
| 6,604,421 B1 * | 8/2003 | Li | 73/636 |
| 7,054,762 B2 | 5/2006 | Pagano et al. | |
| 7,305,885 B2 * | 12/2007 | Barshinger et al. | 73/602 |
| 2009/0282923 A1 * | 11/2009 | Havira | 73/636 |

* cited by examiner

*Primary Examiner*—Jacques M Saint Surin
(74) *Attorney, Agent, or Firm*—Erickson, Kernell, Derusseau & Kieypas, LLC

(57) ABSTRACT

An apparatus for ultrasonic inspection of an object. A tire is mounted for rolling along the surface of the object. It contains a liquid and a transducer assembly. The transducer assembly is positioned in the tire adjacent a portion of the surface of the tire in contact with the object. The liquid and the surface of the tire in contact with the object provide an acoustic bridge between the transducer assembly and the object. An electric signal processing system is connected to the transducer assembly. It generates electric signals which are converted to acoustic signals in the transducer assembly to place acoustic signals in the object. Acoustic signals returned from the object are converted to electric signals by the transducer assembly, and are processed in the electric signal processing system to indicate flaws in the object.

17 Claims, 4 Drawing Sheets

APPARATUS FOR DETECTING, IDENTIFYING AND RECORDING THE LOCATION OF DEFECTS IN A RAILWAY RAIL

FIELD

The present invention relates, in general, to an improvement in nondestructive type testing for certain predetermined types of undesirable flaws and/or other detrimental type defects which may be present in at least one of the rail portions of a railroad track structure and, more particularly, the present invention relates to a mobile type apparatus that will ultrasonically detect these detrimental flaws and/or other type defects in such rail portion and then identify with a mark the location of such defects when they are detected by such apparatus and, additionally, record the particular location of such defects that have been detected for possible future reference and, still more specifically, the instant invention relates to a relatively fast and reliable method of detecting, identifying and recording the location of such undesirable defects that are detected by the apparatus as it travels over the rail.

BACKGROUND

During their normal use and as would be expected, the rail portions of most track structures will be subjected to severe, and uncontrollable environmental conditions. These severe environmental conditions, over a relatively long period of time, may ultimately result in such rail developing certain detrimental flaws. Such flaws may include, for example, cracks.

In addition, in today's modern railroad industry, the rail portion of such track structures will quite often be required to support rather heavy loads being carried by modern freight cars. Furthermore, these heavy loads are travelling at relatively high speeds. It would not be uncommon for these freight cars, when they are fully loaded with cargo, to weigh up to generally about 125 tons. Such relatively heavy loads and high speeds can, also, result in undesirable damage to such rail portions of the track structure. Such damage, for example, may include stress fractures.

It would be expected, therefore, that if these detrimental defects were not timely detected and, likewise, if they are left unrepaired such defects could lead to some rather catastrophic disasters, such as, a train derailment.

As is equally well known, such train derailments are not only costly to the railroad industry from the standpoint of the damage that will likely be incurred to both the cargo being transported and to the railway equipment itself, but, even more importantly, such train derailments may also involve some rather serious injuries, or even worse death, to railway personnel and/or other persons who may be in the vicinity of a train derailment.

It is further well known that a relatively large number of these train derailments have resulted in the undesirable and often costly evacuation of nearby homes and businesses. Such evacuation may be required, for example, when the cargo being transported involves certain highly hazardous chemical products. These hazardous chemical products will generally include both certain types of liquids, such as corrosive acids, and certain types of toxic gases, such as chlorine.

To detect such flaws and defects, ultrasonic testing has been employed. Vehicles have been built which travel along the track and continuously perform ultrasonic testing of the track. These vehicles carry test units which apply ultrasonic signals to the rails, receive ultrasonic signals back from the rails, and provide indications of flaws and defects.

Some of these test units employ sleds which slide along the rails. Acoustic transducers are located in the sleds. These transducers apply ultrasonic signals to the rails, and receive ultrasonic signals back from the rails.

Water is applied to the rails ahead of the sleds to serve as an acoustic bridge between the sleds and the rails. This approach has the disadvantage that it has not been possible to obtain good, constant acoustic contact between the sleds and the rails in heavily curve worn rail. Also such sleds require large amounts of water for adequate sled to rail coupling.

Another approach is to employ small, thin-walled tires which roll along the rails. They are pressed down against the rail so as to have a flat area in contact with the rail. These tires contain acoustic transducers and are filled with a liquid, usually a water-antifreeze solution. The transducers are arranged in an arc to produce acoustic beams which travel through the liquid and are directed toward the center of the flat area. The high frequency electrical transducers are pulsed with energy and the beams intersect in the flat area. The beams then pass through the material of the tire into the rail, are reflected from defects in the rail, the reflected beams returning to the transducers and being detected.

This approach has one disadvantage that only a few transducers can be located in the arc due to spatial considerations. Also, the angles of the acoustic beams produced by the transducers are dictated by their positions in the arc. Another disadvantage is that when the beams strike the inside surface of the tire at the center of the flat area, they generate reflections which cause echoes which reverberate for some time. This limits the times during which signals obtained back from the transducers can be used as indications of beams reflected back from defects and imperfections in the rail.

An additional disadvantage is that for some observations, precise control of the angle of the acoustic beams in the rail is required. This is particularly true for beams which travel along the rail at shallow angles. In this approach, since the beams are generated in liquid, and then, after passing through the tire material, continue in the steel, the beams are refracted by the differing indices of refraction of the acoustic beam between the liquid and steel. Hence, the angle of refraction is affected by the speed of sound in the liquid. For most compositions, this speed depends on the temperature, so the angle of the refracted beam depends on the temperature. To prevent this, it is necessary to use a weak anti-freeze solution for which the speed of sound is temperature invariant. With this weak solution, it is not possible to operate in cold weather.

U.S. Pat. No. 6,055,862 discloses a method of and an apparatus for detecting, identifying and recording the location of defects in a railway rail, which is incorporated herein by reference. The '862 patent discloses a method and apparatus for ultrasonic inspection of an object. A tire is mounted for rolling along the surface of the object. It contains a liquid and a transducer assembly. The transducer assembly is positioned in the tire adjacent a portion of the surface of the tire in contact with the object. The liquid and the surface of the tire in contact with the object provide an acoustic bridge between the transducer assembly and the object. An electric signal processing system is connected to the transducer assembly. It generates electric signals which are converted to acoustic signals in the transducer assembly to place acoustic signals in the object. Acoustic signals returned from the object are converted to electric signals by the transducer assembly, and are processed in the electric signal processing system to indicate flaws in the object.

A problem with some of these prior art systems is that the placement of the transducers may be adversely affected by the defects in the rail which the system is trying to detect. For example, shelling along the gauge side of the rail head may mask defects in the rail. Additionally, gauge face wear may further reduce the effectiveness of transducers located near the typical running surface.

SUMMARY

The present invention provides an improved apparatus for detecting, providing an identification mark and recording the location of certain types of defects detected in an object. Such apparatus includes engagement means such as a tire for rolling contact with the object, the tire containing a liquid. Means are connected to the tire for supporting it and for rolling it along the object. An improved acoustic transducer assembly is located inside the tire. Means are connected to the improved transducer assembly to position it in the tire which is in contact with the object. The liquid provides a coupling between the improved transducer assembly and the tire. In addition, the liquid acts as an acoustic bridge between the improved acoustic transducer assembly and the tire. An electric signal processing means is connected to the improved transducer assembly, the improved transducer assembly providing conversion of energy between electric signals in the electric signal processing means and acoustic signals in the object. The electric signals are for placing acoustic signals in the object and/or for interpretation of acoustic signals returned from the object.

DETAILED DESCRIPTION

Prior to proceeding to the more detailed description of the present invention, it should be noted that for the sake of clarity and understanding of the invention, identical components having identical functions have been identified with identical reference numerals throughout the several views that have been illustrated in the attached drawings.

Figure 1A:
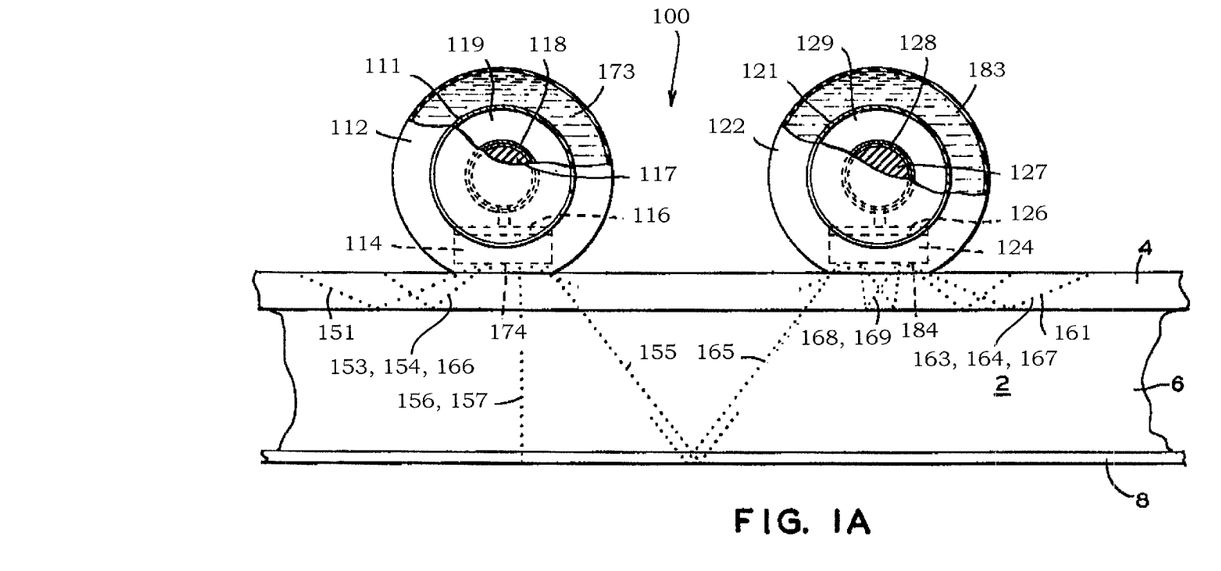
FIG. 1A is a schematic elevation view illustrating an improved two-tired ultrasonic testing assembly used to observe defects in a railroad rail.
Figure 1B:
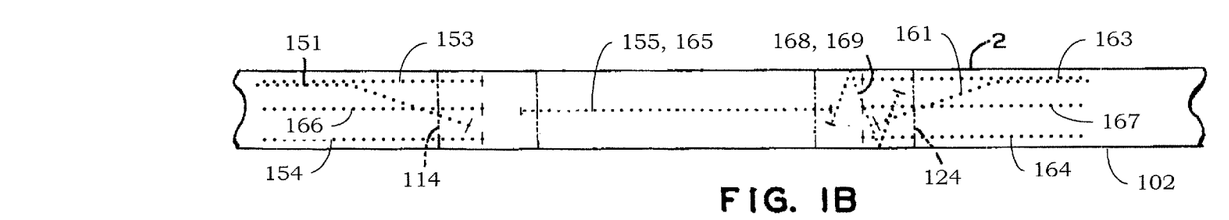
FIG. 1B is a top view of the rail showing the paths followed by various acoustic beams in the rail.

Referring initially to FIGS. 1A, 1B, and 1C, an embodiment of the improved apparatus for detecting, identifying and recording the location of defects in a railway rail is generally indicated by reference numeral 100. The improved apparatus includes a rail engagement means which includes two tires, first tire 112 and second 122. Tire 112 contains liquid 173 and tire 122 contains liquid 183.

Tire 112 may be clamped or otherwise coupled to wheel 119 at its bead 111. Wheel 119 rotates with tire 112 about axle 117 at bearing 118. Axle 117 serves as a support means to place wheel 119 in an operating position with respect to the object being examined. A seal (not shown) concentric with bearing 118 may be provided to permit relative rotation of wheel 119 and axle 117 without loss of coupling liquid from the interior space of tire 112.

Tire 122 may be clamped to the wheel 129 at its bead 121. Wheel 129 rotates with tire 122 about axle 127 at bearing 128. Axle 127 serves as a support means to place wheel 129 in an operating position with respect to the object being examined. A seal (not shown) concentric with bearing 128 is provided to permit relative rotation of wheel 129 and axle 127 without loss of coupling liquid from the interior space of tire 122.

Transducer assembly 114 may be positioned within the first tire 112 by positioning means 116, which may be attached to axle 117. Similarly, transducer assembly 124 may be positioned within the second tire 122 by positioning means 126, which may be attached to axle 127.

Acoustic beams produced by transducers positioned in transducer assemblies 114 and 124 are shown in FIGS. 1A and 1B.

Acoustic beam 151 is directed generally parallel to rail 2 from transducer assembly 114. Viewed from above, as in FIG. 1B, the beam 151 crosses the rail 2 at an angle of about 10 to 30 degrees. Viewed in transverse section FIG. 1A, the beam 151 descends into the rail 2 at an angle of about 60 to 80 degrees from the vertical. This beam 151 provides a view of under shell defects, since it approaches the under shell defects from underneath.

In the prior art embodiment disclosed in U.S. Pat. No. 6,055,862, two beams 51 and 52 also provided a view of the under shell defects. However, because the shelling and wear typically occurs on the gauge side of the rail 2 and can cover a relatively large portion of the rail head 4, the gauge side beam 52 may not be able to penetrate the rail head 4. The shelling can totally block the beam 52 and because of the relatively close spacing of the transducers 33 and 34, also block or obscure beam 51.

Accordingly, in a present embodiment a transducer 133 which generates beam 151 may be placed closer to the field edge 102 of the rail head 4. By being placed closer to the field edge 102 of the rail head 4, the beam 151 has clearer steel outside the area prone to shelling through which to enter the rail head 4. From there, the beam 151 continues to the gauge corner where it can pocket and reflect on fissures resulting from shelled areas that may be turned downward. This placement of transducer 133 outside the typical running surface also helps alleviate the effect of gauge-face wear. This arrangement may also be more sensitive to detecting relatively small fissures formed high in the gauge corner, weld materials, and shelled areas that are starting to progress in a transverse plane.

Acoustic beam 161 may also be directed approximately parallel to rail 2 from transducer assembly 124. Viewed from above, as in FIG. 1B, beam 161 crosses the rail at an angle of about 10 to 30 degrees. Viewed in transverse section FIG. 1A, beam 161 descends into the rail 2 at an angle of about 60 to 80 degrees from the vertical. This beam 161 provides a view of under shell defects, since it approaches the under shell defects from underneath.

Acoustic beams 153, 154 and 166 when viewed from above are seen to be parallel to the rail 2, but in elevation view FIG. 1A, they are seen to descend into the rail 2 at an angle of about 60 to 80 degrees from the vertical. The beams 153, 154 and 166 and look substantially down the rail 2 and may be used in conjunction with views from beam 151.

In contrast to beams 53, 54, 63 and 64 from transducers 33, 34, 43 and 44 respectively shown in the '862 patent, acoustic beams 153, 154 and 166 from transducers 133, 134 and 146 face in opposite directions from acoustic beams 163, 164 and 167 from transducers 143, 144 and 147 to avoid interference, false returns and for spacing considerations.

Acoustic beams 163 and 164 when viewed from above are seen to be parallel to the rail 2, but in elevation view FIG. 1A, they are seen to descend into the rail 2 at an angle of about 60 to 80 degrees from the vertical. The beams 163 and 164 look substantially down the rail 2 and may, for example, be used in conjunction with views from beam 161.

Beams 155 and 165 are generated by transducers 135 and 145, respectively. These beams 155 and 165 penetrate through the web 6 of rail 2 to the bottom 8 of rail 2. They show defects in the web 6 including bolt hole cracks. Beams 155 and 165, also, show weld defects and centrally located transverse defects. These beams 155 and 165 are transmitted toward each other from the two transducers 135 and 145.

Beams 156 and 157 descend in a substantially vertical direction from the transducer assembly 114 through web 6 to the bottom 8 of rail 2. Such beams 156 and 157 act as one channel. Beams 156 and 157, like beams 155 and 165 show web 6 defects, including bolt hole cracks, as well as rail head 4 and web 6 horizontals and angled defects.

Beams 168 and 169 are, also, produced by the transducer assembly 124. They examine the rail head 4. Such beams 168 and 169 are directed downward at approximately 60 to 80 degrees to the vertical, and viewed from above, are inclined at about 5 to 15 degrees to the transverse axis of the rail 2.

Figure 2:
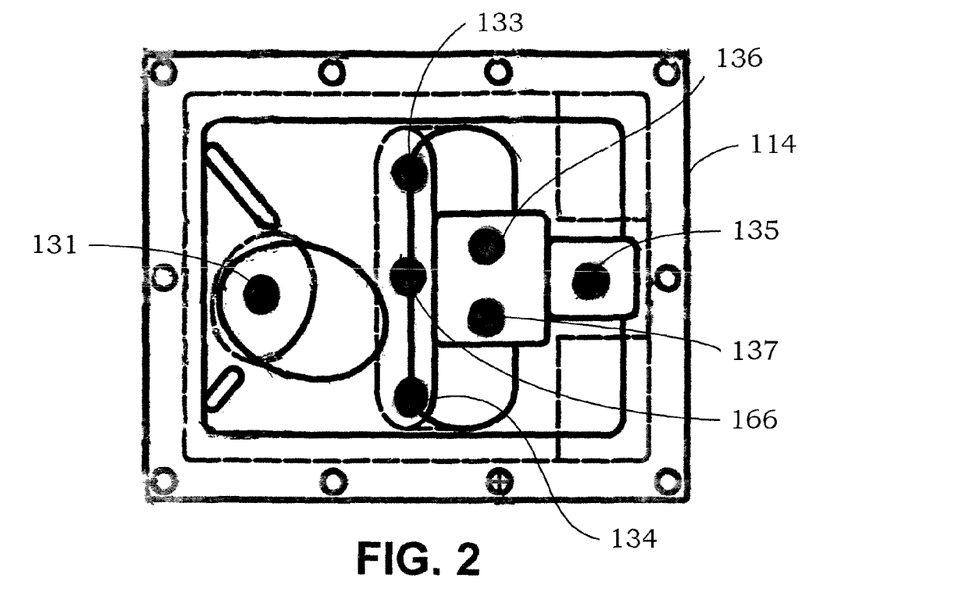
FIG. 2 is a schematic top view illustrating an acoustic transducer assembly module used in a first one of the two tires.

FIG. 2 is a schematic top view of transducer assembly 114. Transducer assembly 114 is attached to a positioning means 116 at flange 113. Transducer 131 generates the beam 151. Transducers 133 and 134 generate beams 153 and 154, respectively. Transducer 135 generates the beam 155 and transducer 136 generates the beam 156. Transducer 137 generates the beam 157.

Figure 3:
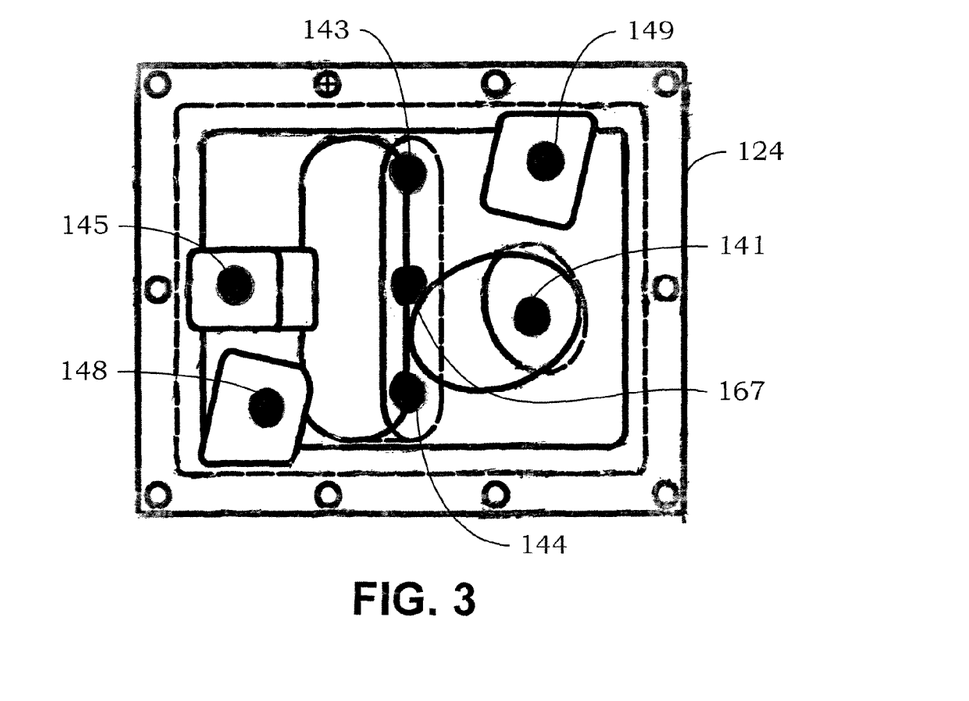
FIG. 3 is a schematic top view illustrating an acoustic transducer assembly module used in a second one of the two tires.

FIG. 3 is a schematic top view of transducer assembly 124. Transducer 141 generates beam 161. Transducers 143 and 144 generate beams 163 and 164, respectively. Transducer 145 generates the beam 165. Transducers 146 and 147 generate the beams 166 and 167. Transducer 148 generates beam 168 and the transducer 149 generates beam 169.

Figure 4:
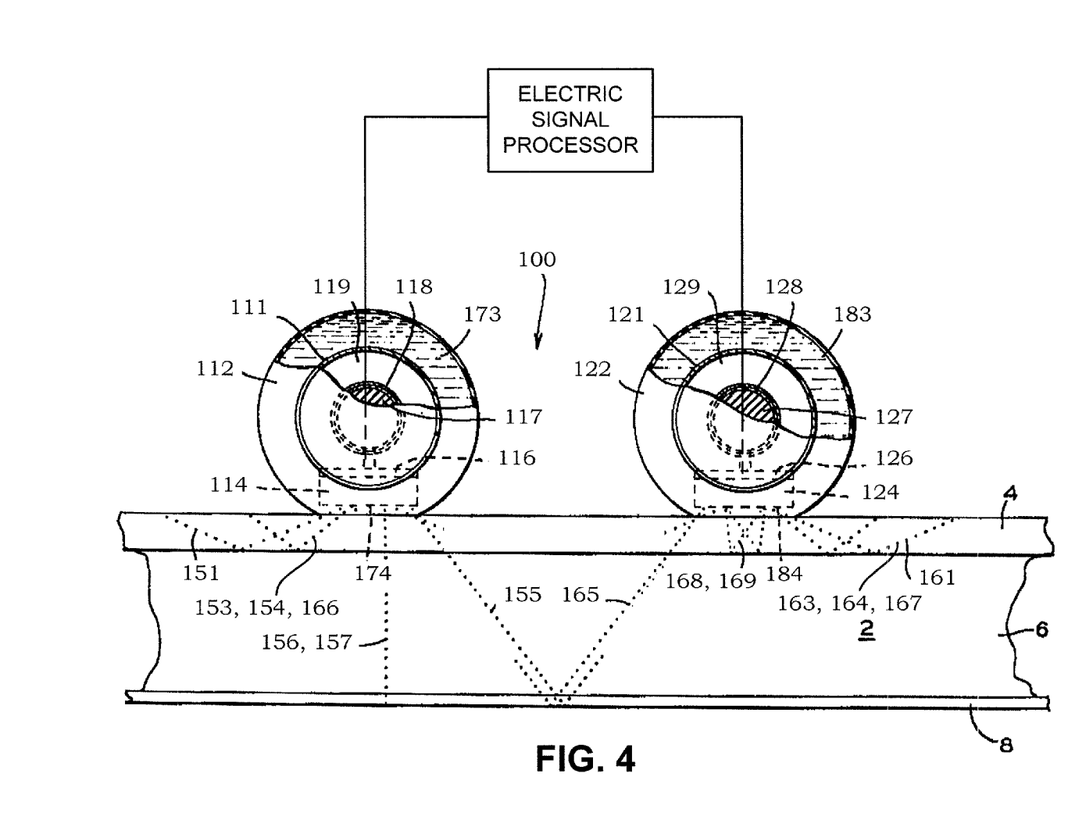
FIG. 4 shows cabling from the transducers to the electric signal processing means.

The transducers are connected to electric signal processing means by cables 170 and 172 (shown in FIGS. 4 & 5) which pass through the axles 117 and 127. The transducers in transducer assembly 114 are connected by cable 170 through axle 117 to electric signal processing means 179. Likewise, the transducers in transducer assembly 124 are connected by cable 172 through axle 127 to electric signal processing means 179.

The transducer assemblies 114 and 124 may be plastic blocks which have sockets machined therein into which the transducers are mounted. The presently preferred material employed for the blocks will be chosen for its easy machining properties and for its excellent stability in a water-based environment.

The sockets may be formed with flat bottom surfaces on which the transducers are cemented, for example, by an epoxy resin. It is necessary to have a good acoustic connection between the transducers and the blocks.

The sockets may be machined with a variety of orientations, which depend upon the orientation of the acoustic beams which are required. The acoustic beam is transmitted generally perpendicular to the flat on which the transducer is mounted.

For the acoustic beams for which precise control of angle is required, notably beams 151, and 161, the beam from the transducer passes first through the plastic to encounter the bottom surface of the plastic of the block, then through a layer of liquid, then through the thickness of the tire material, and then finally into the rail 2. FIG. 1B shows bottom surface 174 of transducer assembly 114, and bottom surface 184 of transducer assembly 124.

The electric signal processing means is responsible for generating the high frequency pulses of electric energy which energize the transducers. The electric signal processing means are also responsible for interpreting the electric signals returned from the transducers, which contain information regarding defects in the rail 2. Such electric signal processing means may provide indications of defects such as directing a paint spraying means to mark defective area of the rail 2. The electric signal processing means may also provide a display to an operator of the vehicle, or store the information in a memory storage device. In the latter case, navigational information, such as data from a global positioning system or milepost data may be recorded along with information regarding defects.

Figure 5:
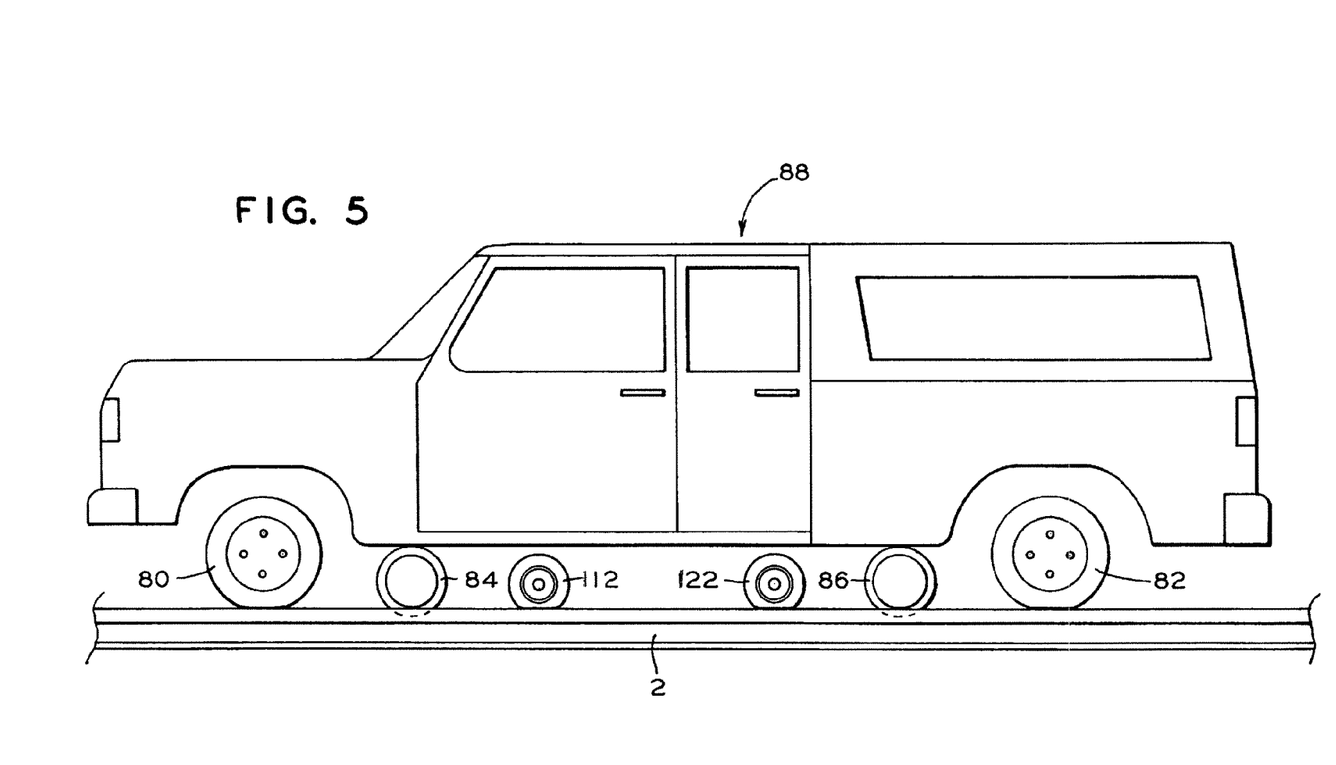
FIG. 5 illustrates a test vehicle with the improved two-tired ultrasonic testing assembly of FIG. 1A.

FIG. 5 shows vehicle 188 with tires 112 and 122 containing sensors. The vehicle has rubber tires 180 and 182 and flanged wheels 184 and 186 which serve as guide means for keeping the vehicle on the rails. Tires 112 and 122 and guide means 184 and 186 are lifted when the vehicle is driven off the rails.

Now discussing the invention more broadly, there is disclosed an apparatus for detecting, providing indications and recording the location of certain types of defects detected in an object. Such apparatus includes an engagement means consisting of a tire for rolling contact with the object, the tire containing a liquid. Means are connected to the tire for supporting it and for rolling it along the object. An acoustic transducer assembly is located inside the tire. Means are connected to the transducer assembly to position it in the tire adjacent a part of the tire in contact with the object. The liquid acts as an acoustic bridge between the acoustic transducer assembly and the tire. An electric signal processing means is connected to the transducer assembly. The transducer assembly provides conversion of energy between electric signals in the electric signal processing means and acoustic signals in the object. The electric signals are for placing acoustic signals in the object and/or for interpretation of acoustic signals returned from the object.

The object observed for defects by this apparatus may be elongated, in which case acoustic beams may be defined in relation to a major axis of the object. Beams may, for example be applied to the object, the beams directed at a predetermined angle relative to the major dimension of the object. They may, for example, be approximately parallel to the object. The beam may also have a direction at a predetermined angle relative to a minor dimension of the object.

The electric signal processing means may generate pulses of high frequency electric energy followed by quiet times. The transducers converting the pulses of high frequency electric energy into pulses of ultrasonic acoustic energy. The pulses of ultrasonic energy coupled into the object return acoustic signals from the object containing information regarding imperfections in the object. The transducers convert the returned acoustic energy into return electric signals which provide information regarding imperfections in the object. The apparatus may also include means for displaying signals indicating such imperfections in the object.

The acoustic transducer assembly may be formed from a block of plastic having a pocket formed in it and a planar surface in the pocket and a transducer cemented against the planar surface to provide good acoustic contact between the transducer and the block. The planar surface of the pocket may be machined at a predetermined angle relative to the surface which contacts the inside surface of the tire to provide a predetermined direction for the acoustic beam in the plastic block and hence a predetermined direction for the beam refracted into the object.

In another aspect, the invention provides for ultrasonic inspection of one or more rails of a pair of railroad rails. The apparatus includes a vehicle which can travel along the pair of rails. It has an engagement means consisting of a tire attached to the vehicle for rolling contact with one of the rails. The tire contains a liquid and a transducer assembly. Means is attached to the vehicle for positioning the transducer assembly inside the tire. The liquid and the portion of the tire in contact with the rail acting as an acoustic bridge between the transducer assembly and the rail. An electric signal processing means is located on the vehicle and connected to the transducer assembly. The transducers serve to convert energy between electric signals in the electric signal processing means and acoustic signals in the rail, the electric signals for placing acoustic signals in the rail and/or for interpreting acoustic signals returned from the rail.

The apparatus may include at least one transducer oriented at a predetermined angle relative to the lengthwise dimension of the rail. The transducer interchanges electric energy between the electric signal processing means and acoustic signals in the rail. The acoustic signals having a predetermined orientation relative to the lengthwise dimension of the rail. The predetermined orientation of the transducer would be determined considering refraction between the block and the rail. The beam direction may be approximately parallel to the lengthwise dimension of the rail.

The beam may be angled downward and be reflected from the lower surface of the rail head (above the web of the rail). It would be reflected upward to illuminate deep imperfections which would otherwise be obscured by surface imperfections in the rail. The surface imperfections, for example, may be shelling, which is laminar cracks just under the wear surface of the rail, which are caused by fatigue cycling due to passage of load bearing wheels.

One transducer may be used to create a beam in the rail which crosses the centerline of the rail at a small angle, while descending to bounce off the lower surface of the rail head to illuminate deep imperfections which would otherwise be obscured by surface imperfections. This transducer may be positioned close to the field side of the rail head to avoid possibly shelled areas and gauge-face wear.

The apparatus may further include a transducer mounted at a predetermined angle relative to the widthwise dimension of the rail. This transducer interchanges energy between electric signals in the electric signal processing means and an acoustic beam in the rail, which has a predetermined direction relative to the widthwise dimension of the rail.

The electric signal processing means produces pulses of high frequency electric energy followed by quiet times. The transducer assembly converts the pulses of high frequency electric energy into pulses of ultrasonic energy, which are coupled into the rail. The transducer assembly also receives acoustic energy back from the rail. The acoustic energy indicating imperfections in the rail, the transducer assembly converting the acoustic energy into electrical signals which the electric signal processing means uses to generate signals indicative of imperfections. Means may be provided for these to be displayed.

The transducer assembly may be formed from a block of plastic with a pocket formed in it, the pocket having a planar surface onto which a transducer is cemented for good acoustic contact between the transducer and the block. The planar surface in the pocket is inclined at a predetermined angle relative to the bottom surface, so that the transducer cemented into the pocket projects an acoustic beam oriented at a predetermined angle for refraction into the rail at a predetermined angle.

The apparatus may also include a transducer which projects a beam downward for reflection of the lower surface of the rail head on one side of the rail, and is bounced approximately horizontally to bounce off the lower surface of the rail head on the other side of the rail and then upward to another transducer. This arrangement provides for detecting flaws at the elevation of the bottom of the rail head. Such a flaw, for example, could be a vertically split head.

The apparatus may further include a transducer which sends an acoustic beam downward through the web to be reflected off the bottom surface of the rail. Such a beam may detect flaws in the longitudinal or horizontal plane such as a split web.

The apparatus may include a pair of tires mounted in tandem on the same rail. A transducer disposed in one of the tires would project a beam downward and toward the other tire, the beam penetrating the web, bouncing off the lower surface of the rail, and being detected by the transmitting transducer. This would provide observation of flaws in the web such as bolt hole cracks.

The vehicle on which this system is preferably mounted on rubber tires so that it can drive onto or off of the rails which the system is to examine. The vehicle includes guide means disposed thereon which can contact the gauge surface of the rails to guide the tires and keep the vehicle on the rails. These guide means would be elevated when the vehicle operates off the rails. The tire or tires containing the transducers would also be elevated for travel off the rails, to prevent contact between these tires and the terrain.

In an additional aspect, this invention provides a method for ultrasonic inspection of an object. The method includes rolling an engagement means such as a tire along the surface of the object. The tire contains both a liquid and a transducer assembly. The transducer assembly is placed adjacent a portion of the tire in contact with the surface of the object. The liquid provides an acoustic bridge between the transducer assembly and the tire. The transducer assembly has at least one transducer which is firmly attached to it.

The method includes applying high frequency electrical pulses to the transducer to induce it to generate ultrasonic pulses which create ultrasonic beams which pass through the transducer assembly, the liquid and the tire into the object. The beam encounters imperfections in the object and generates back reflected acoustic signals which indicates the imperfections. The back reflected acoustic signals returning to the transducer to generate electric signals which indicate the imperfections. The method includes transmitting the electric signals which indicate imperfections to an electric signal processing means which then defines and provides indication of the imperfections.

The object being examined may be an elongate object and it may be a rail of a railroad. In this case, the ultrasonic beam is projected into the rail at a direction which is approximately parallel to the centerline of the rail. The ultrasonic beam may be projected at an angle sloping downward to be reflected off the lower surface of the rail head to produce an upward reflected beam which illuminates deep defects otherwise hidden underneath surface imperfections. These deep defects providing a back reflected acoustic signal. The method may also include projecting such a beam across the width of the rail head to bounce off the lower surface of the rail head on opposite sides of the rail to illuminate deep defects on the opposite sides of the rail. The method may further include projecting two such beams, projected from opposite sides of the rail to the opposing sides of the rail at the lower surfaces of the rail head, thereby illuminating deep defects on both sides of the rail.

The method may also include projecting a beam steeply downward on the centerline of the rail to illuminate the web and bottom flange of the rail, and the method may include receiving a reflected acoustic signal which shows imperfections in the web and bottom flange of the rail.

While both a presently preferred and various alternative embodiments of the invention have been described in detail above it should be recognized that various other adaptations and modifications of the invention may be made by those persons skilled in the rail testing art without departing from either the spirit of the invention or the scope of the appended claims.

Having thus described the invention, what is claimed as new and desired to be secured by Letters Patent is:

1. In an ultrasonic testing device for detecting flaws in a railway rail having a rail head with a center line, a field side and a gauge side, the ultrasonic testing device comprising an engagement means mounted to be in rolling contact with the railway rail, at least one transducer mounted within the engagement means, means connected to the at least one transducer for providing electrical signals for generation of at least one acoustic beam, and means connected to the at least one transducer for receiving signals indicative of a reflected acoustic signal and outputting an electrical signal, and for processing the electrical signals to provide signals indicative of such flaws in such railway rail, wherein the improvement comprises:

said at least one transducer mounted within said engagement means at a position closer to the field side of the railway rail than the gauge side of the railway rail at a first angle of between 10 and 30 degrees from generally parallel to the center line from the field side to the gauge side of the rail head, and at a second angle of between 60 and 80 degrees from vertical;

wherein said acoustic beam generated by said at least one transducer enters the rail head on the field side of the center line and continues across the rail head to the gauge side of the center line; and wherein said at least one transducer receives signals indicative of a reflected acoustic signal from said acoustic beam and outputs an electrical signal for processing.

2. The improvement of claim 1 further comprising a second transducer mounted within said engagement means at a position generally parallel to the center line of said railway rail and proximal the field side of the railway rail at an angle of between 60 and 80 degrees from vertical, wherein said second transducer generates a second acoustic beam, receives signals indicative of a reflected acoustic signal from said second acoustic beam and outputs a second electrical signal for processing.

3. The improvement of claim 2 further comprising a third transducer mounted within said engagement means at a position generally parallel to the center line of said railway rail and proximal the gauge side of the railway rail at an angle of between 60 and 80 degrees from vertical, wherein said third transducer generates a third acoustic beam, receives signals indicative of a reflected acoustic signal from said third acoustic beam and outputs a third electrical signal for processing.

4. The improvement of claim 3 further comprising a fourth transducer mounted within said engagement means at a position generally collinear with the center line of said railway rail at an angle of between 60 and 80 degrees from vertical, wherein said fourth transducer generates a fourth acoustic beam, receives signals indicative of a reflected acoustic signal from said fourth acoustic beam and outputs a fourth electrical signal for processing.

5. The improvement of claim 4 further comprising a second engagement means mounted to be in rolling contact with the railway rail at a position spaced from said engagement means, a fifth transducer mounted within the second engagement means, means connected to the fifth transducer for providing electrical signals for generation of a fifth acoustic beam, and means connected to the fifth transducer for receiving signals indicative of a reflected acoustic signal and outputting an electrical signal to be processed, said fifth transducer mounted within said second engagement means at a position closer to the field side of the railway rail than the gauge side of the railway rail at a first angle of between 10 and 30 degrees from generally parallel to the center line from the field side to the gauge side of the rail head, and at a second angle of between 60 and 80 degrees from vertical and facing in a direction relative to the railway rail opposite said at least one transducer, wherein said fifth acoustic beam generated by said fifth transducer enters the rail head on the field side of the center line and continues across the rail head to the gauge side of the center line.

6. The improvement of claim 5 further comprising a sixth transducer mounted within said second engagement means at a position generally parallel to the center line of said railway rail and proximal the field side of the railway rail at an angle of between 60 and 80 degrees from vertical and facing in a direction relative to the railway rail opposite said second transducer, wherein said sixth transducer generates a sixth acoustic beam, receives signals indicative of a reflected acoustic signal from said sixth acoustic beam and outputs a sixth electrical signal for processing.

7. The improvement of claim 6 further comprising a seventh transducer mounted within said second engagement means at a position generally parallel to the center line of said railway rail and proximal the gauge side of the railway rail at an angle of between 60 and 80 degrees from vertical and facing in a direction relative to the railway rail opposite said third transducer, wherein said seventh transducer generates a seventh acoustic beam, receives signals indicative of a reflected acoustic signal from said seventh acoustic beam and outputs a seventh electrical signal for processing.

8. The improvement of claim 7 further comprising a eighth transducer mounted within said second engagement means at a position generally collinear with the center line of said railway rail at an angle of between 60 and 80 degrees from vertical and facing in a direction relative to the railway rail opposite said fourth transducer, wherein said eighth transducer generates a eighth acoustic beam, receives signals indicative of a reflected acoustic signal from said eighth acoustic beam and outputs a eighth electrical signal for processing.

9. In an ultrasonic testing device for detecting flaws in a railway rail having a rail head with a center line, a field side and a gauge side, the ultrasonic testing device comprising at least one tire mounted to be in rolling contact with the railway rail, at least one transducer mounted within the at least one tire, means connected to the at least one transducer for providing electrical signals for generation of at least one acoustic beam, and means connected to the at least one transducer for receiving electrical signals indicative of a reflected acoustic signal, and for processing the electrical signals to provide signals indicative of such flaws in such railway rail, wherein the improvement comprises:

said at least one transducer mounted within the at least one tire at a position closer to the field side of the railway rail than the center line of the railway rail at a first angle of between 10 and 30 degrees from generally parallel to the center line from the field side to the gauge side of the rail head, and at a second angle of between 60 and 80 degrees from vertical;

wherein said acoustic beam generated by said at least one transducer enters the rail head on the field side of the center line and continues across the rail head to the gauge side of the center line; and wherein said at least one transducer receives signals indicative of a reflected acoustic signal from said acoustic beam and outputs an electrical signal for processing.

10. The improvement of claim 9 further comprising a second transducer mounted within said at least one tire at a position generally parallel to the center line of said railway rail and proximal the field side of the railway rail at an angle of between 60 and 80 degrees from vertical, wherein said second transducer generates a second acoustic beam, receives signals indicative of a reflected acoustic signal from said second acoustic beam and outputs a second electrical signal for processing.

11. The improvement of claim 10 further comprising a third transducer mounted within said at least one tire at a position generally parallel to the center line of said railway rail and proximal the gauge side of the railway rail at an angle of between 60 and 80 degrees from vertical, wherein said third transducer generates a third acoustic beam, receives signals indicative of a reflected acoustic signal from said third acoustic beam and outputs a third electrical signal for processing.

12. The improvement of claim 11 further comprising a fourth transducer mounted within said at least one tire at a position generally collinear with the center line of said railway rail at an angle of between 60 and 80 degrees from vertical, wherein said fourth transducer generates a fourth acoustic beam, receives signals indicative of a reflected acoustic signal from said fourth acoustic beam and outputs a fourth electrical signal for processing.

13. The improvement of claim 12 further comprising a second tire mounted to be in rolling contact with the railway rail at a position spaced from said at least one tire, a fifth transducer mounted within the second tire, means connected to the fifth transducer for providing electrical signals for generation of a fifth acoustic beam, and means connected to the fifth transducer for receiving signals indicative of a reflected acoustic signal and outputting an electrical signal to be processed, said fifth transducer mounted within said second tire at a position closer to the field side of the railway rail than the gauge side of the railway rail at a first angle of between 10 and 30 degrees from generally parallel to the center line from the field side to the gauge side of the rail head, and at a second angle of between 60 and 80 degrees from vertical and facing in a direction relative to the railway rail opposite said at least one transducer, wherein said fifth acoustic beam generated by said fifth transducer enters the rail head on the field side of the center line and continues across the rail head to the gauge side of the center line.

14. The improvement of claim 13 further comprising a sixth transducer mounted within said second tire at a position generally parallel to the center line of said railway rail and proximal the field side of the railway rail at an angle of between 60 and 80 degrees from vertical and facing in a direction relative to the railway rail opposite said second transducer, wherein said sixth transducer generates a sixth acoustic beam, receives signals indicative of a reflected acoustic signal from said sixth acoustic beam and outputs a sixth electrical signal for processing.

15. The improvement of claim 14 further comprising a seventh transducer mounted within said second tire at a position generally parallel to the center line of said railway rail and proximal the gauge side of the railway rail at an angle of between 60 and 80 degrees from vertical and facing in a direction relative to the railway rail opposite said third transducer, wherein said seventh transducer generates a seventh acoustic beam, receives signals indicative of a reflected acoustic signal from said seventh acoustic beam and outputs a seventh electrical signal for processing.

16. The improvement of claim 15 further comprising an eighth transducer mounted within said second tire at a position generally collinear with the center line of said railway rail at an angle of between 60 and 80 degrees from vertical and facing in a direction relative to the railway rail opposite said fourth transducer, wherein said eighth transducer generates a eighth acoustic beam, receives signals indicative of a reflected acoustic signal from said eighth acoustic beam and outputs a eighth electrical signal for processing.

17. In an ultrasonic testing device for detecting flaws in a railway rail having a rail head with a center line, a field side and a gauge side, the ultrasonic testing device comprising a first tire mounted to be in rolling contact with the railway rail, a second tire mounted to be in rolling contact with the railway rail at a position spaced from said first tire, a plurality of transducers mounted within the first and second tires, means connected to the plurality of transducers for providing electrical signals for generation of acoustic beams, and means connected to the plurality of transducers for receiving electrical signals indicative of reflected acoustic signals, and for processing the electrical signals to provide signals indicative of such flaws in such railway rail, wherein the improvement comprises:

a first transducer mounted within the first tire at a position closer to the field side of the railway rail than the gauge side of the railway rail at a first angle of between 10 and 30 degrees from generally parallel to the center line from the field side to the gauge side of the rail head, and at a second angle of between 60 and 80 degrees from vertical, wherein said first transducer generates a first acoustic beam which enters the rail head on the field side of the center line and continues across the rail head to the gauge side of the center line, and wherein said first transducer receives signals indicative of a reflected acoustic signal from said first acoustic beam and outputs a first electrical signal for processing;

a second transducer mounted within said first tire at a position generally parallel to the center line of said railway rail and proximal the field side of the railway rail at an angle of between 60 and 80 degrees from vertical, wherein said second transducer generates a second acoustic beam, receives signals indicative of a reflected acoustic signal from said second acoustic beam and outputs a second electrical signal for processing;

a third transducer mounted within said first tire at a position generally parallel to the center line of said railway rail and proximal the gauge side of the railway rail at an angle of between 60 and 80 degrees from vertical, wherein said third transducer generates a third acoustic beam, receives signals indicative of a reflected acoustic signal from said third acoustic beam and outputs a third electrical signal for processing;

a fourth transducer mounted within said first tire at a position generally collinear with the center line of said railway rail at an angle of between 60 and 80 degrees from vertical, wherein said fourth transducer generates a fourth acoustic beam, receives signals indicative of a reflected acoustic signal from said fourth acoustic beam and outputs a fourth electrical signal for processing;

a fifth transducer mounted within the second tire at a position closer to the field side of the railway rail than the gauge side of the railway rail at a first angle of between 10 and 30 degrees from generally parallel to the center line from the field side to the gauge side of the rail head, and at a second angle of between 60 and 80 degrees from vertical and facing in a direction relative to the railway rail opposite said first transducer, wherein said fifth acoustic beam generated by said fifth transducer enters the rail head on the field side of the center line and continues across the rail head to the gauge side of the center line, and wherein said fifth transducer receives signals indicative of a reflected acoustic signal from said fifth acoustic beam and outputs a fifth electrical signal for processing;

a sixth transducer mounted within the second tire at a position generally parallel to the center line of said railway rail and proximal the field side of the railway rail at an angle of between 60 and 80 degrees from vertical and facing in a direction relative to the railway rail opposite said second transducer, wherein said sixth transducer generates a sixth acoustic beam, receives signals indicative of a reflected acoustic signal from said sixth acoustic beam and outputs a sixth electrical signal for processing;

a seventh transducer mounted within said second tire at a position generally parallel to the center line of said railway rail and proximal the gauge side of the railway rail at an angle of between 60 and 80 degrees from vertical and facing in a direction relative to the railway rail opposite said third transducer, wherein said seventh transducer generates a seventh acoustic beam, receives signals indicative of a reflected acoustic signal from said seventh acoustic beam and outputs a seventh electrical signal for processing; and an eighth transducer mounted within said second tire at a position generally collinear with the center line of said railway rail at an angle of between 60 and 80 degrees from vertical and facing in a direction relative to the railway rail opposite said fourth transducer, wherein said eighth transducer generates a eighth acoustic beam, receives signals indicative of a reflected acoustic signal from said eighth acoustic beam and outputs a eighth electrical signal for processing.

* * * * *